(12) United States Patent
Grossi et al.

(10) Patent No.: US 7,951,952 B2
(45) Date of Patent: May 31, 2011

(54) METHOD FOR PREPARING N-AMINOPIPERIDINE AND ITS SALTS

(75) Inventors: Pierre Jean Grossi, Aramon (FR); Raphael Sole, Comps (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/164,379

(22) Filed: Jun. 30, 2008

(65) Prior Publication Data

US 2008/0306274 A1 Dec. 11, 2008

Related U.S. Application Data

(63) Continuation of application No. 11/625,367, filed on Jan. 22, 2007, now abandoned, which is a continuation of application No. PCT/FR2005/002016, filed on Aug. 2, 2005.

(30) Foreign Application Priority Data

Aug. 5, 2004 (FR) ..................... 04 08700

(51) Int. Cl.
*C07D 211/00* (2006.01)
(52) U.S. Cl. ...................................... 546/244
(58) Field of Classification Search ........... 546/244
See application file for complete search history.

(56) References Cited

U.S. PATENT DOCUMENTS

| 3,317,607 A | 5/1967 | Latourette, et. al. |
| 5,514,806 A | 5/1996 | Rrbczynski et al. |

FOREIGN PATENT DOCUMENTS

| DE | 338609 | 6/1921 |
| EP | 0850930 | 7/1998 |
| JP | 2004137181 | 5/2004 |
| JP | 2004137182 | 5/2004 |

OTHER PUBLICATIONS

Brehme, R., et. al., Aza-enamines. VIII. Electrophilic Substitution Reactions at the Azomethine Carbon Atom of Aldehyde Dialkylhydrazones: Vilsmeier Formylation and Consecutive Reactions, Chemische Berichte (1990) vol. 123, No. 10, pp. 2039-2046.
Bustos, Q.M., et. al., Compounds of 1-Amino Piperidine with Divalent Cadmium, Cobalt, Nickel, and Copper Ions, Revista de La Real Academia De Ciencias Exactas, Fisicas Y Naturales De Madrid (1969) vol. 63, pp. 627-635.
Katritzky, A.R., et. al., A Novel and Versatile Synthesis of 1-alkyl-, 1-(alkylamino)-, or 1-amido-substituted and 1,2,6-trisubstituted piperidines from Glutaraldehyde and Primary amines or Monosubstituted Hydrazines, Org. Chem. vol. 55, (1990) pp. 3205-3209.
Lunn, G., et. al., Reduction of Nitrosamines with Aqueous Titanium Trichloride; Convenient Preparation of Aliphatic Hydrazines, Journal of Organic Chemistry (1984) vol. 49, No. 19, pp. 3470-3473.
Ohme, R., et. al., Hydrazines and Azo Compounds from Diamides of Sulfuric Acid, Justus Liebigs Annalen Der Chemie (1968) vol. 713, pp. 74-86.
Hinman, et. al., Alkylation of Acylhydrazines. The Synthesis of Trimethylamine-Benzimide, Journal of the American Chemical Society, (1959), vol. 24, pp. 660-664.
Salman, M., et. al., Studies iin antifertility agents: Part XXXVI—Syntheses of N-(substituted benzylidene) aminophthalimides, -dihydroisoindoles and -1,2,3,4-tetrahydroisoquinolines, Indian Journal of Chemistry, Section B: Organic Chemistry including Medicinal Chemistry, (1981), 20B(6), pp. 477-479.

*Primary Examiner* — Taylor Victor Oh
(74) *Attorney, Agent, or Firm* — Scully, Scott, Murphy & Presser, P.C.

(57) ABSTRACT

The invention concerns a novel method for preparing N-aminopiperidine of formula (I):

(I)

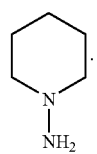

15 Claims, No Drawings

METHOD FOR PREPARING N-AMINOPIPERIDINE AND ITS SALTS

CROSS REFERENCE TO RELATED APPLICATIONS

This application is a continuation of U.S. application Ser. No. 11/625,367, filed Jan. 22, 2007, now abandoned, which is a continuation of International application No. PCT/FR2005/002,016, filed Aug. 2, 2005, both of which are incorporated herein by reference in their entirety; which claims the benefit of priority of French Patent Application No. 04/08,700, filed Aug. 5, 2004.

BACKGROUND OF THE INVENTION

1. Field of the Invention

A subject-matter of the present invention is a novel process for the preparation of N-aminopiperidine of formula

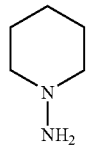

(I)

2. Description of the Art

Several processes for the preparation of N-aminopiperidine are known in the literature:
  Raschig process using piperidine and chloramine;
  process via hydrazine and N-acetylamino-piperidine;
  process via N-nitrosopiperidine (Lunn, Keefer, J. Org. Chem., 1984, 49 (19), 3470);
  process via glutaraldehyde and benzotriazole (Katritzky A. R., Wei-Quiang Fan, J. Org. Chem., 1990, 55, 3205-3209).

All of the references described herein are incorporated herein by reference in their entirety.

SUMMARY OF THE INVENTION

The process for the preparation of N-aminopiperidine (I) and its salts according to the present invention is characterized in that:
  a) a carbazate of formula:

(II)

in which R represents a $(C_1-C_6)$alkyl group, a phenyl or a benzyl, is treated with a 1,5-dihalopentane of formula:

(III)

in which Hal represents a halogen atom;
  b) the piperidin-1-ylcarbamate thus obtained of formula:

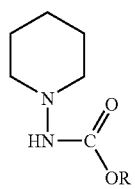

(IV)

in which R represents a $(C_1-C_6)$alkyl group, a phenyl or a benzyl, is treated in acidic medium or in basic medium to produce the expected N-aminopiperidine.

If appropriate, a salt of N-aminopiperidine (I) can be prepared by the action of an inorganic or organic acid.

DETAILED DESCRIPTION OF THE INVENTION

The term "halogen atom" is understood to mean a bromine, chlorine or iodine atom.

Stage a) is carried out in a solvent, such as acetonitrile or toluene, at a temperature between ambient temperature and the reflux temperature of the solvent.

Stage b) is carried out either in acidic medium, for example in the presence of hydrochloric or hydrobromic acid, or in basic medium, for example in the presence of potassium hydroxide or sodium hydroxide, in a solvent such as water or ethanol and at a temperature between ambient temperature and the reflux temperature of the solvent.

According to a preferred embodiment of the present invention, in stage a), a compound of formula (II) in which R represents an ethyl radical is treated with a compound of formula (III) in which Hal represents a bromine atom, in acetonitrile, by heating at reflux of the solvent.

According to a preferred embodiment of the present invention, in stage b), the compound of formula (IV) in which R represents an ethyl radical is treated with sodium hydroxide in water by heating at reflux of the solvent.

Preferably, an N-aminopiperidine salt, such as the hydrobromide, the hydrochloride or the oxalate, is prepared. For example, N-aminopiperidine hydrobromide can be prepared in a solvent such as methyl tert-butyl ether (MTBE).

EXAMPLE

A—Ethyl piperidin-1-ylcarbamate

A mixture of 565.3 g of ethyl carbazate in 373 ml of acetonitrile is prepared. 415.4 g of 1,5-dibromopentane are run onto the preceding mixture brought to reflux. Reflux is maintained for 3 hours. The acetonitrile is removed by concentrating under vacuum. The residue thus obtained is dissolved in a toluene/water mixture. The two-phase mixture is brought to pH=5 by addition of 30% NaOH. The aqueous phase is separated by settling and re-extracted with toluene. Water and 36% HCl are added to the combined toluene phases. The "rich" aqueous phase is washed 3 to 4 times with methyl tert-butyl ether (MTBE) to remove the neutral materials (impurities, diethyl carbazate, residual dibromopentane). The acidic aqueous phase is basified with NaOH and then NaHCO₃ in the presence of toluene. The aqueous phase is re-extracted with toluene. The toluene phases are washed separately with water in order to remove any residual ethyl carbazate. The toluene phases are concentrated to dryness. 252 g of the expected product are obtained in the form of a white powder which is purified by recrystallization from methylcyclohexane.

$^1$H NMR spectrum at 300 MHz: δ (ppm): 1.23: t: 3H, 4.14: qd: 2H, 2.70: t: 4H, 1.66: qt: 4H, 1.36: qt: 2H, 5.54: bs: 1H.

B—N-Aminopiperidine

A mixture of 160 g of compound obtained in the preceding stage, 214 ml of water and 120 g of sodium hydroxide beads is brought to reflux for 3 hours while flushing with argon. After cooling, 640 ml of MTBE are introduced before filtering off the inorganic materials present. A crude N-aminopiperidine solution in MTBE is thus obtained.

C—Preparation of Crude N-Aminopiperidine Hydrobromide

Approximately 1 volume of a 36% w/w solution of hydrobromic acid in ethanol is run, at 25° C. and over 0.5 hour, onto the solution of N-aminopiperidine in MTBE obtained in the preceding stage. The formation of a precipitate is observed and the mixture is kept stirred for 1 hour. The hydrobromide is filtered off at 20° C. and washed with ethanol and then with MTBE. It is subsequently dried under vacuum at 45-50° C. and 156 g of the expected compound are obtained.

M.p.=177-177.5° C. (literature 174-175° C.).

What is claimed is:

1. A process for the preparation of N-aminopiperidine of formula (I):

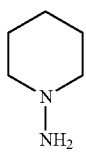

(I)

or a salt thereof, comprising the steps of:
a) reacting a carbazate of formula (II):

in which R represents a $(C_1-C_6)$alkyl group, a phenyl or a benzyl, with a 1,5-dihalopentane of formula (III):

in which Hal represents a halogen atom to obtain piperidin-1-ylcarbamate of formula (IV):

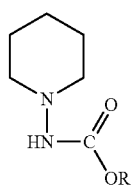

(IV)

in which R is as defined above;
b) treating the piperidin-1-ylcarbamate thus obtained in basic medium to produce the compound of formula (I); and
c) reacting the compound of formula (I) taken in a solvent with a suitable inorganic or organic acid to form the salt of the compound of formula (I).

2. The process according to claim 1, wherein in step a), the reaction is carried out in a solvent chosen from acetonitrile or toluene at a temperature in the range of from about ambient temperature and about reflux temperature of the solvent.

3. The process according to claim 1, wherein in step b), the reaction is carried out using a base chosen from potassium hydroxide or sodium hydroxide in a solvent chosen from water or ethanol and at a temperature in the range of from about ambient temperature and about reflux temperature of the solvent.

4. The process according to claim 2, wherein in step b), the reaction is carried out using a base chosen from potassium hydroxide or sodium hydroxide in a solvent chosen from water or ethanol and at a temperature in the range of from about ambient temperature and about reflux temperature of the solvent.

5. The process according to claim 1, wherein, in step a), a compound of formula (II) in which R represents an ethyl radical is treated with a compound of formula (III) in which Hal represents a bromine atom, in acetonitrile, by heating at reflux of the solvent.

6. The process according to claim 1, wherein, in step b), the compound of formula (IV) in which R represents an ethyl radical is treated with sodium hydroxide in water by heating at reflux of the solvent.

7. The process according to claim 1, wherein in step c), the compound of formula (I) is reacted with an inorganic acid to form the salt.

8. The process according to claim 7, wherein the inorganic acid is chosen from hydrochloric acid or hydrobromic acid.

9. The process according to claim 1, wherein in step c), the compound of formula (I) is reacted with an organic acid to form the salt.

10. The process according to claim 9, wherein the organic acid is oxalic acid.

11. The process according to claim 1, wherein in step c), the solvent is methyl tert-butyl ether.

12. The process according to claim 1, wherein in step c), the reaction is carried out in the temperature range of from about 0° C. to about 40° C.

13. The process according to claim 1, wherein in step c), the reaction is carried out at a temperature of about 25° C.

14. The process according to claim 1, wherein a salt of the compound of formula (I) chosen from the hydrobromide, the hydrochloride or the oxalate is prepared.

15. The process according to claim 1, wherein the hydrobromide of the compound of formula (I) is prepared in methyl tert-butyl ether.

* * * * *